United States Patent [19]

Voss et al.

[11] 4,335,114
[45] Jun. 15, 1982

[54] 1-N-ALKYLSISOMICIN DERIVATIVES, THEIR PRODUCTION AND THEIR MEDICINAL USE

[75] Inventors: Eckart Voss, Cologne; Karl G. Metzger, Wuppertal; Hans-Joachim Zeiler, Velbert; Uwe Petersen, Leverkusen; Peter Stadler, Haan, all of Fed. Rep. of Germany

[73] Assignee: Bayer Aktiengesellschaft, Leverkusen, Fed. Rep. of Germany

[21] Appl. No.: 161,527

[22] Filed: Jun. 20, 1980

[30] Foreign Application Priority Data

Jul. 12, 1979 [DE] Fed. Rep. of Germany ....... 2928183

[51] Int. Cl.³ .................. A61K 31/71; C07H 15/22
[52] U.S. Cl. .................................. 424/180; 536/13.9
[58] Field of Search .................. 424/180; 536/17 R

[56] References Cited

U.S. PATENT DOCUMENTS

| | | | |
|---|---|---|---|
| 3,925,353 | 12/1975 | Umezawa et al. | 536/17 |
| 4,002,742 | 1/1977 | Wright et al. | 536/17 |
| 4,048,431 | 9/1977 | Hlavka et al. | 536/4 |
| 4,085,208 | 4/1978 | Mallams et al. | 536/17 |

FOREIGN PATENT DOCUMENTS

| | | | |
|---|---|---|---|
| 2240015 | 7/1975 | France | 536/17 R |
| 2355029 | 2/1978 | France | 536/17 R |

*Primary Examiner*—Johnnie R. Brown
*Attorney, Agent, or Firm*—Sprung, Horn, Kramer & Woods

[57] ABSTRACT

The invention relates to sisomicin derivatives defined below in Formula (I) and a process for the preparation of said derivatives. Also included in the invention are compositions containing said derivatives and methods for using said derivatives and compositions.

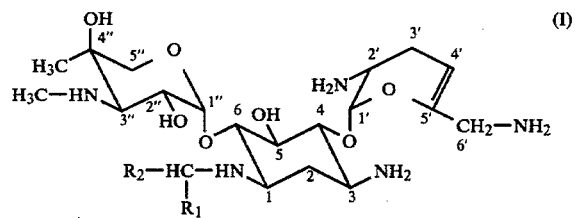

17 Claims, No Drawings

1-N-ALKYLSISOMICIN DERIVATIVES, THEIR PRODUCTION AND THEIR MEDICINAL USE

The present invention relates to sisomicin derivatives, to a process for their production and to their use as medicaments.

Sisomicin and its derivatives which have hitherto been disclosed belong to the class of aminoglycoside antibiotics. Aminoglycoside antibiotics are important substances for effectively combating bacterial infections. However, in many cases the occurrence of resistant germs reduces their broad applicability; moreover, side-effects, such as ototoxicity and nephrotoxicity, can occur. In some cases, it is possible to eliminate these disadvantages by forming derivatives. Thus, aminoglycoside antibiotics which are substituted on the 1-amino group by $-CH_2X$ radicals have already been disclosed, inter alia, in DE-OS (German Published Specification No.) 2,437,160.

According to the present invention there are provided compounds which are sisomicin derivatives of the general formula

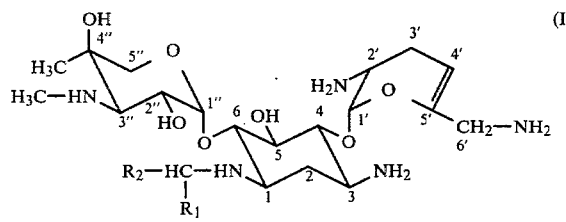

or a salt thereof, in which $R_1$ and $R_2$ independently denote a $C_1$ to $C_6$ alkyl group optionally substituted with the condition that the radical

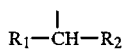

cannot simultaneously carry an amino group and a hydroxyl group as substituents.

The compounds of the present invention can avoid the above-mentioned disadvantages of sisomicin and known sisomicin derivatives to a particularly great extent.

Possible substituents of the alkyl radicals $R_1$ and $R_2$ are, preferably, hydroxyl, $C_1$ to $C_4$ alkoxy, amino, $C_1$ to $C_4$ alkylamino, di-$C_1$ to $C_4$ alkylamino, acyloxy, acylamino, N-$C_1$ to $C_4$ alkyl-N-acylamino, carboxyl, ($C_1$ to $C_4$ alkoxy)-carbonyl, aminocarbonyl, $C_1$ to $C_4$ alkylaminocarbonyl or di-$C_1$ to $C_4$ alkyl-aminocarbonyl, acyl being, preferably ($C_1$ to $C_4$ alkyl)-carbonyl.

Preferably, $R_1$ denotes a $C_1$ to $C_6$ alkyl group which is optionally substituted by hydroxyl, and more preferably denotes methyl or hydroxymethyl, and $R_2$ denotes $C_1$ to $C_6$ alkyl which is optionally monosubstituted to pentasubstituted by hydroxyl or carboxyl, wherein no more than a single hydroxyl or carboxyl substituent is present on any alkyl carbon atom.

The compounds according to the invention and their pharmaceutical usable salts exhibit powerful and antibacterial properties against a large number of germs, and an exceptionally good tolerance.

Among the new sisomicin derivative salts of the invention, those salts that are pharmaceutically accept-able (and especially pharmaceutically acceptable acid-addition salts) are particularly important and are preferred.

The new free sisomicin derivatives of the general formula I and their salts can be interconverted in any suitable manner; methods for such interconversion are known in the art.

The pharmaceutically usuable salts are derived, preferably, from inorganic or organic acids, such as sulphuric acid, phosphoric acid, nitric acid, hydrochloric acid, hydrobromic acid, acetic acid, propionic acid, pamoic acid, ascorbic acid and citric acid.

Examples of suitable radicals $R_1$ and $R_2$ are prop-2-yl, 1-hydroxyprop-2-yl, 4-hydroxybut-2-yl, 5-hydroxypent-2-yl, 4-hydroxycyclohex-1-yl, 3,4-dihydroxybut-2-yl, 4,5-dihydroxy-pent-2-yl, 1,3-dihydroxyprop-2-yl, 1,3,4-trihydroxybut-2-yl, 1,3,4,5-tetrahydroxypent-2-yl, 1,3,4,5,6-pentahydroxyhex-2-yl, piperidin-4-yl, 1-aminoprop-2-yl, 4-aminobut-2-yl, 5-aminopent-2-yl and 1,7-diaminohept-4-yl.

The above-mentioned radicals are to be understood only as examples. In most cases, they contain at least one or more chiral carbon atoms. It can be advantageous to prepare and use the compounds according to the invention as optically pure products. Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

According to the present invention there is further provided a process for the production of a compound of the present invention in which a selectively acylated or sulphenylated compound of the general formula

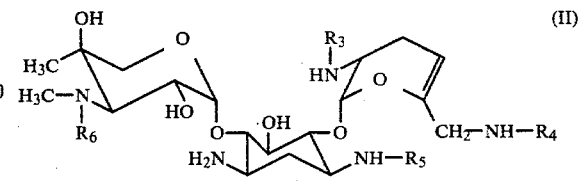

in which $R_3$, $R_4$, $R_5$ and $R_6$ independently denote -SR' or -CO-R'', in which R' denotes an optically substituted phenyl or di- or tri-phenylmethyl radical and R" denotes -(CH$_2$)$_{n_1}$-B or

in which

B denotes a hydrogen atom or an optionally substituted phenyl radical, and n$_1$, n$_2$, n$_3$ and n$_4$ independently of one another are 0, 1, 2, 3, 4 or 5, is reacted with a carbonyl compound of the general formula $$R_2-\overset{O}{\underset{\|}{C}}-R_1 \quad (III)$$

in which R$_1$ and R$_2$ have the meaning indicated above, and in which any amino and alkylamino substituted on R$_1$ and R$_2$ are protected by R'-S- or R"-CO-groups wherein R' and R" have the meaning indicated above, R$_2$ are protected by R'-S- or R"-CO- groups, in the presence of a hydrogen donor reducing agent and the protective groups -S-R' or -CO-R" are then split off.

The optionally substituted phenyl radical R' is, preferably a phenyl radical, or a phenyl radical which is substituted by 1 to 3 substituents selected from nitro, C$_1$ to C$_4$-alkyl, C$_1$ to C$_4$-alkoxy, (C$_1$ to C$_4$ alkoxy)-carbonyl and phenyl, or by 1 to 5 halogen atoms.

The optionally substituted phenyl radical B is, preferably a phenyl radical, or a phenyl radical which is substituted by 1 or 2 substituents selected from nitro, C$_1$ to C$_4$ alkoxy, phenyl and halogen.

Starting substances of the formula (II) which are used are preferably 2',3,3",6'-tetra-N-(o-nitrophenylsulphenyl)-sisomicin, 3"-N-(o-nitrophenylsulphenyl)-2',3,6'-tris-N-trichloroacetylsisomicin, 3"-N-(o-nitrophenylsulphenyl)-2',3,6'-tris-N-trifluoroacetylsisomicin, 3"-N-(o-nitrophenylsulphenyl)-2',3,6'-tris-N-(2,2,2-trichloroethoxycarbonyl)-sisomicin, 3"-N-(o-nitrophenylsulphenyl)-2'3,6'-tris-N-(1,1-dimethyl-2,2,2-trichloroethoxycarbonyl)-sisomicin, 3"-N-(o-nitrophenylsulphenyl)-2',3,6'-tris-N-(4-methoxybenzyloxycarbonyl)-sisomicin, 3"-N-(o-nitrophenylsulphenyl)-2',3,6'-tris-N-phenoxycarbonylsisomicin and 3"-N-(o-nitrophenylsulphenyl)-2',3,6'-tris-N-(tert.-butoxycarbonyl)-sisomicin, the preparation of which is carried out by the process described in DE-OS (German Published Specification No.) 2,726,197, or via the following stages:

(1) reaction of penta-N-(o-nitrophenylsulphenyl)-sisomicin (DE-OS (German Published Specification No.) 2,726,197) with dimethyl-(1,2-dimethyl-propyl)-silyl chloride to give penta-N-(o-nitrophenyl-sulphenyl)-2"-O-[dimethyl-(1,2-dimethylpropyl)-silyl]-sisomicin;

(2) splitting off of the o-nitrophenylsulphenyl groups from the 2'-, 3- and 6'-N with 2-mercaptobenzthiazole;

(3) acylation of the 2'-, 3- and 6'-positions with a customary acylating agent;

(4) splitting off of the 2"-O-protective group and (5) splitting off of the 1-N-(o-nitrophenylsulphenyl) group.

The reductive alkylation with a carbonyl compound of the formula (III) in the presence of a hydrogen donor reducing agent is usually carried out at room temperature in the presence of air, although it can be more favourable to carry out the reaction under an inert gas, such as argon or nitrogen. The reaction usually goes to completion very rapidly, frequently in less than 60 minutes, which can be established by determination by thin layer chromatography.

Hydrogen donor reducing agents which are used in this process include dialkylaminoboranes, for example dimethylaminoborane, diethylaminoborane and morpholinoborane; tetraalkylammonium cyanoborohydrides, for example tetrabutylammonium cyanoborohydride; alkali metal borohydrides, for example sodium borohydride; and, preferably, alkali metal cyanoborohydrides, such as lithium cyanoborohydride and sodium cyanoborohydride.

The process is usually carried out in an inert solvent. The solvent can be an organic or inorganic solvent, in which the selectively protected sisomicin and the other reagents are soluble and which as far as possible reduces or prevents side reactions under the reaction conditions. Although anhydrous aprotic solvents, for example tetrahydrofurane, can advantageously be employed if the reducing agent is morpholinoborane, a protic solvent is nevertheless usually used. A suitable protic solvent is, for example, a C$_1$ to C$_6$ alkanol or, preferably, water or an aqueous C$_1$ to C$_6$ alkanol, preferably aqueous methanol or ethanol, or acetone or other solvent systems which contain water, such as aqueous dimethylformamide, aqueous hexamethylphosphoramide, aqueous tetrahydrofurane or aqueous ethylene glycol dimethyl ether.

The process is usually carried out in a pH range of 1 to 11, and preferably 4 to 8.

The carbonyl compounds used in the process are either known or they are accessible by known syntheses. In some cases, carbonyl compounds with chiral carbon atoms are available as optically pure compounds, especially if they are keto-sugars. They can be employed for the reductive alkylation either in the free form or as ketals, for example as dimethyl ketals. If ketals are used, the reaction is carried out in the presence of a mineral acid or an organic acid, such as acetic acid, whereupon the ketal is split and the carbonyl compound liberated reacts immediately with the appropriate amino group of the sisomicin.

Specific examples of the active compounds according to the invention which may be mentioned are: 1-N-(prop-2-yl)-sisomicin, 1-N-(1-hydroxyprop-2-yl)-sisomicin, 1-N-(4-hydroxybut-2-yl)-sisomicin, 1-N-(5-hydroxypent-2-yl)-sisomicin, 1-N-(4-hydroxycyclohex-1-yl)-sisomicin, 1-N-(3,4-dihydroxybut-2-yl)1-sisomicin, 1-N-(4,5-dihydroxypent-2-yl)-sisomicin, 1-N-(1,3-dihydroxyprop-2-yl)-sisomicin, 1-N-(1,3,4-trihydroxybut-2-yl)-sisomicin, 1-N-(1,3,4,5-tetrahydroxypent-2-yl)-sisomicin, 1-N-(1,3,4,5,6-pentahydroxyhex-2-yl)-sisomicin, 1-N-(piperidin-4-yl)-sisomicin, 1-N-(3-aminoprop-2-yl)-sisomicin, 1-N-(4-amino-but-2-yl)-sisomicin, 1-N-(5-aminopent-2-yl)-sisomicin and 1-N-(1,7-diaminohept-4-yl)-sisomicin.

The compounds according to the invention are antimicrobial agents with a broad spectrum of action and a particular activity against Gram-negative bacteria. These properties enable them to be used as medicaments, in particular in combating illnesses, in warm-blooded animals, caused by bacteria.

They are particularly suitable for the chemotherapy, in medicine, of local and systemic infections, in particular infections of the urogenital system which are caused by Gram-negative bacteria, for example E. coli, Proteus, Klebsiella and Pseudomonas, Inhibition areolae in the agar hole test were found, for example, against the following strains of bacteria at a concentration of 100 micrograms/1 ml: Pseudomonas aerug. 5737, Pseudomonas aerug. F 41, Klebsiella pneum. 2 Munich, Klebsiella pneum. 1 Düsseldorf, E. coli Münster and E. coli Neumann.

As stated above, the invention also relates to the use in medicine of the compounds of the invention.

The present invention provides a pharmaceutical composition containing as active ingredient a compound of the invention in admixture with a solid, liquid or liquid gaseous diluent.

The invention further provides a pharmaceutical composition containing as active ingredient a compound of the invention in the form a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention. "Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol and $C_{16}$-fatty acid]) or mixtures of these diluents.

The pharmaceutical compositions which are ointments pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For application to ears and eyes or for parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention when in the form of topical preparations generally contain from 0.1 to 3.0 g of the active ingredient per 100 g of ointment, cream or lotion.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally, intramuscularly or topically. Preferred pharmaceutical compositions and medicaments are therefore those adapted for administration such as oral, intramuscular or topical administration. Administration in the method of the invention is preferably oral, intramuscular or topical administration.

The dosage of the compounds according to the invention is usually similar to the dosage of the 1-N-unsubstituted compounds. The dosage range is generally 20 mg/day/animal in 2,000 mg/day/animal, preferably 100 mg-500 mg/day.

Topical application, in the form of ointment, cream or lotion having the content of active compound previously mentioned, is generaly effected 2 to 5 times daily.

Injection solutions or suspensions are usually administered such that the infected organism receives about 1 to 15 mg of active compound per kilogram of body weight, in 2 to 4 doses per day.

Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered it can be advisable to divide these into several individual administrations over the course of the day.

The compounds of the present invention may also be administered by being admixed to animal feed. The present invention thus provides a medicated feed comprising a compound of the present invention and a nutritious material.

The following formulations illustrate pharmaceutical compositions according to the present invention.

| Formulation 1 | | |
|---|---|---|
| Tablet | 10 mg tablet | 100 mg tablet |
| (a) 1-N-[1-Hydroxyprop-2-yl]-sisomicin | 10.50+ mg | 105.50+ mg |
| Lactose | 197.50 mg | 126.00 mg |
| Maize starch | 25.00 mg | 35.00 mg |
| Polyvinylpyrrolidone | 7.50 mg | 7.50 mg |
| Magnesium stearate | 2.50 mg | 3.50 mg |

+5% excess

To prepare the tablets, a suspension of the active compound in question, lactose and polyvinylpyrrolidone is prepared and this spray-dried. The maize starch and magnesium stearate are added and the mixture is pressed to tablets.

| Formulation 2 | |
|---|---|
| Ointment | |
| 1-N-[1-Hydroxyprop-2-yl]-sisomicin | 1.0 g |
| Methylparaben U.S.P. | 0.5 g |
| Propylparaben U.S.P. | 0.1 g |
| Petrolatum | to 1,000 g |
| Preparation | |

(1) The petrolatum is melted; (2) the active compound, Methylparaben and Propylparaben are mixed with about 10% of the molten petrolatum, (3) the mixture is introduced into a colloid mill and (4) the remaining petrolatum is added, whilst stirring, and the mixture is cooled until it becomes semi-solid. The product is filled into suitable containers.

| Formulation 3 | | |
|---|---|---|
| Injection solution | per 2.0 ml phial | per 50 liters |
| 1-N-[1-Hydroxyprop-2-yl]-sisomicin | 84.0 mg+ | 2,100.0 gm |
| Methylparaben, U.S.P. | 3.6 mg | 90.0 gm |
| Propylparaben, U.S.P. | 0.4 mg | 10.0 gm |
| Sodium bisulphite, U.S.P. | 6.4 mg | 160.0 gm |
| Disodium ethylenediamine-tetraacetate dihydrate | 0.2 mg | 5.0 gm |
| Water, U.S.P. q.s. | 2.0 mg | 50.0 liters |

+5% excess

The following Examples illustrate the production of compounds according to the present invention.

EXAMPLE 1

Penta-N-(o-nitrophenylsulphenyl)-2''-O-[dimethyl-(1,2-dimethylpropyl)-silyl]-sisomicin 60.6 g of crude penta-N-(o-nitrophenylsulphenyl)-sisomicin and 8.75 g of imidazole are dissolved in 250 ml of absolute methylene chloride. 22.5 ml of dimethyl-(1,2-dimethyl-propyl)-silyl chloride are added dropwise at 0° C., with exclusion of moisture. The batch is evaporated to about 170 ml in vacuo and is left to stand at room temperature for 48 hours. After adding 130 ml of absolute methylene chloride, the precipitate is filtered off, the filtrate is vigorously shaken thoroughly with 350 ml of petroleum ether and the petroleum ether phase is decanted off and discarded. The oil which has separated out is dissolved in 100 ml of methylene chloride, separated out again with 250 ml of petroleum ether and finally dried under a high vacuum. Yield: 60 g (89%) of crude product, which can be employed for the subsequent reactions without further purification. A pure product is obtained by chromatography on silica gel using CH$_2$Cl$_2$/CH$_3$OH=99/1.

R$_F$ (CH$_2$Cl$_2$/CH$_3$OH=99.5/0.5): 0.62

13-C-NMR (CDCl$_3$): δ=124–138 (aromatic C); 147.54

(C-5'); 102.26 (C-1''); 97.81 (C-4'); 99.09 (C-1'); -2.9 to -3.0 (Si-CH$_3$); 22.77

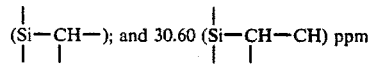

Penta-N-(o-nitrophenylsulphenyl)-2'',5-bis-O-[dimethyl-(1,2-dimethyl-propyl)-silyl]-sisomicin is isolated as a by-product.

R$_F$ (CH$_2$Cl$_2$/CH$_3$OH=99.5/0.5): 0.79

13-C-NMR (CDCl$_3$): δ=124–146 (aromatic C); 148.00 (C-5'); and 96.13 (C-4') ppm

EXAMPLE 2

1.3''-Bis-N-(o-nitrophenylsulphenyl)-2''-O-[dimethyl-(1,2-dimethyl-propyl)-silyl]-sisomicin 16 g of 2-mercapto-benzthiazole are added to 56 g of crude penta-N-(o-nitrophenylsulphenyl)-2''-O-[dimethyl-(1,2-dimethyl-propyl)-silyl]-sisomicin in 36 ml of methylene chloride/70 ml of methanol and the mixture is shaken until a clear solution is obtained and is left to stand at 5° C. for 2 hours. The precipitate which thereby separates out is filtered and the solution is used for the subsequent reactions without isolating the desired product. The yield is about 80% of theory. To prepare a pure product, the filtrate is evaporated rapidly in vacuo and the residue is chromatographed on silica gel using (a) methylene chloride, (b) methylene chloride/CH$_3$OH (8:2) and (c) CH$_2$Cl$_2$/CH$_3$OH/20% strength aqueous ammonia (7:2.7:0.3). The yield of pure product is 25.3 g (69%).

R$_F$ (CH$_2$Cl$_2$/CH$_3$OH/20% strength aqueous NH$_3$=7:2.7:0.3)=0.66

13-C-NMR (CD$_3$OD): δ=1.5 (Si-CH$_3$); 122–146 (aromatic C); 147.14 (C-5'); 103.31 (C-1''); 100.16 (C-1') and 99.30 (C-4') ppm 3 g (10%) of 3''-N-(o-nitrophenylsulphenyl)-2''-O-[dimethyl-(1,2-dimethyl-propyl)-silyl]-sisomicin are isolated as a by-product during the column chromatography.

R$_F$ CH$_2$Cl$_2$/CH$_3$OH/20% aqueous NH$_3$=7:2.7:0.3)=0.15

13-C-NMR (CD$_3$OD): δ=76.66 (C-2''); 21.70 (C-6''); 30.40 (N-CH$_3$) 53.13 (C-1); 52.18 (C-3); 44.06 (C-6') and 49.41 (C-2') ppm

EXAMPLE 3

1,3''-Bis-N-(o-nitrophenylsulphenyl)-2',3,6'-tris-N-trichloroacetyl-2''-O-[dimethyl](1,2-dimethyl-propyl)-silyl]-sisomicin 7.5 ml of trichloroacetic anhydride are added dropwise to 8.8 g of 1,3''-bis-N-(o-nitrophenylsulphenyl)-2''-O-[dimethyl-(1,2-dimethyl-propyl)-silyl]-sisomicin in 20 ml of methylene chloride/20 ml of pyridine at −15° C. and the mixture is further stirred, at room temperature, for another 10 minutes. After adding 20 ml of methylene chloride, the batch is twice extracted by shaking with 20 ml of H$_2$O each time, the organic phase is evaporated and the residue is further processed as the crude product. R$_F$ (CH$_2$Cl$_2$/CH$_3$OH=97.5/2.5)=0.72

EXAMPLE 4

1,3''-Bis-N-(o-nitrophenylsulphenyl)-2',3,6'-tris-N-trichloroacetyl-sisomicin

The crude oil from Example 3 is dissolved in 20 ml of dimethylsulphoxide, 2 ml of a 50 percent strength KF solution are added and the mixture is stirred vigorously for 3 hours. The product is precipitated with water, washed with water and dried. The crude product is subsequently processed without further purification.

R$_F$ (CH$_2$Cl$_2$/CH$_3$OH=97.5/2.5)=0.42

13-C-NMR (CDCl$_3$) δ=103.60 (C-1''); 66.48 (C-3''); 55.15 (C-1); 50.60 (C-3); 79.86 (C-4); 76.18 (C-5); 89.16 (C-6); 97.74 (C-1'); 96.84 (C-4'); 149.80 (C-5'); 92.78 (CCl$_3$); and 162.29 and 162.11 (CO) ppm.

EXAMPLE 5

3''-N-(o-nitrophenylsulphenyl)-2',3,6'-tris-N-trichloroacetyl-sisomicin

The product from Example 4 is dissolved in 13 ml of methylene chloride, the solution is shaken with 26 ml of methanol and 5 g of 2-mercaptobenzthiazole until a clear solution is obtained and this solution is left to stand at 5° C. for 3 days. The precipitate is filtered off, the filtrate is evaporated and the residue is chromatographed on silica gel (running agent a: CH$_2$Cl$_2$/CH$_3$OH=95/5; b: CH$_2$Cl$_2$/CH$_3$OH/20% strength aqueous NH$_3$=93/6.5/0.5).

R$_F$: (CH$_2$Cl$_2$/CH$_3$OH/20% strength aqueous NH$_3$=93/6.5/0.5): 0.43

13-C-NMR (CDCl$_3$): δ=103.43 (C-1''); 67.46 (C-3''); 50.85 (C-1); 50.28 (C-3); 79.44 (C-4); 76.51 (C-5); 89.29 (C-6); 97.61 (C-1'); 96.62 (C-4'); 149.50 (C-5'); 92.46 and 92.38 (C-4'); and 162.01 and 161.76 (CO) ppm.

EXAMPLE 6

1-N-(Prop-2-yl)-sisomicin 10 g of 3''-N-(o-nitrophenylsulphenyl)-2',3,6'-tris-N-trichloroacetyl-sisomicin are dissolved in 250 ml of acetone and 46 ml of water, and 4.5 g of BaBH$_3$CN are added in portions. The pH is adjusted to 5 with acetic acid. After 30 minutes, the batch is evaporated in vacuo, the oily residue is taken up in methylene chloride and the methylene chloride mixture is extracted several times by shaking with water. The organic phase is concentrated to 50 ml, 50 ml of saturated methanolic barium hydroxide solution and 30 ml of methanol are added and the mixture is left to stand at room temperature for 10 hours. After evaporating off the solvent in vacuo, 3.4 g of 2-mercapto-benzthiazole in 20 ml of methylene chloride/6 ml of methanol are added to the residue and the mixture is acidified with 4 N sulphuric acid. The aqueous phase is separated off, the precipitate is centrifuged off, the centrifugate is brought to pH 10 with a basic ion exchanger (OH− form) and is evaporated and the residue is chromatographed on silica gel (running agent: CH$_2$Cl$_2$/CH$_3$OH/20% strength aqueous NH$_3$=2/4/1). The main component is isolated by evaporating the appropriate fractions.

R$_f$=0.46 (CH$_2$Cl$_2$/CH$_3$OH/20% strength aqueous NH$_3$=2/4/1).

EXAMPLE 7

1-N-(1-Hydroxyprop-2-yl)-sisomicin 10 g of 3''-N-(o-nitrophenylsulphenyl)-2',3,6'-tris-N-trichloroacetylsisomicin are dissolved in 50 ml of tetrahydrofurane and 15 ml of water, 1.3 ml of hydroxyacetone are added and 1.5 g of $NaBH_3CN$ are added in portions, and the mixture is adjusted to pH 5 with acetic acid. After 20 hours at room temperature, the batch is evaporated in vacuo, the residue is taken up in methylene chloride and the methylene chloride mixture is extracted several times by shaking with water. The organic phase is concentrated to 50 ml and, as described for Example 6, saturated $Ba(OH)_2$ solution and then 2-mercaptobenzthiazole are added. The product formed is purified by chromatography on silica gel, as described for Example 6.

$R_f=0.4$ ($CH_2Cl_2/CH_3OH/20\%$ strength aqueous $NH_3=2/4/1$).

EXAMPLE 8

1-N-(1,3-Dihydroxyprop-2-yl)sisomicin 1.5 g of 3''-N-(o-nitrophenylsulphenyl)-2',3,6'-tris-N-trichloroacetylsisomicin are dissolved in 15 ml of methanol/2.4 ml of water and the solution is brought to pH 5.5 with acetic acid. After adding 250 mg of $NaBH_3CN$ and 300 mg of dihydroxyacetone, the batch is stirred at room temperature for 5 hours and evaporated in vacuo. The residue is taken up in 5.3 ml of methanol and the mixture is added dropwise to 53 ml of water, whilst stirring vigorously. The precipitate is centrifuged off, digested with 20 ml of water, centrifuged off again and dissolved in 25 ml of methanol at 45° C., and 1.35 g of $Ba(OH)_2$ in 7.5 ml of water are added. After 15 hours at room temperature, the batch is diluted with 7.5 ml of water and the barium salts are precipitated by adding solid $CO_2$. The precipitate is filtered off, the filtrate is evaporated and the residue is chromatographed on silica gel (running agent: lower phase of the mixture $CH_2Cl_2/CH_3OH/15\%$ strength $NH_3=1/1/1$).

The orange-coloured fraction is evaporated, the residue is dissolved in 8 ml of methylene chloride/5 ml of methanol, 510 mg of 2-mercaptobenzthiazole in 1.5 ml of $CH_3OH/2.5$ ml of $CH_2Cl_2$ are added and the mixture is brought to pH 1 with 10% strength aqueous HCl. After adding 14 ml of $H_2O$ and 3.5 ml of $CH_2Cl_2$, the aqueous phase is separated off, and is brought to pH 11 by adding further ion exchanger, the ion exchanger is filtered off and the filtrate is evaporated. The product remains as a colourless foam.

$R_f=0.31$ ($CH_2Cl_2/CH_3OH/20\%$ strength aqueous $NH_3=2/4/1$).

EXAMPLE 9

1-N-(5-Hydroxypent-2-yl)-sisomicin 1 g of 3''-N-(o-nitrophenylsulphenyl)-2',3,6'-tris-N-trichloroacetylsisomicin is dissolved in 5 ml of tetrahydrofurane and 1.5 ml of water, and 220 mg of 5-hydroxypentan-2-one and 200 g of $NaBH_3CN$ are added. After adjusting the pH to 5 with acetic acid, the batch is heated to 50° C. for 8 hours and then evaporated, the residue is taken up in methylene chloride and the methylene chloride mixture is twice extracted by shaking with water. The organic phase is concentrated to 5 ml, 5 ml of $CH_3OH$ and 5 ml of saturated methanolic $Ba(OH)_2$ solution are added and the mixture is left to stand at room temperature for 12 hours. After neutralisation with solid $CO_2$, the precipitate is filtered off and the filtrate is chromatographed on silica gel (running agent: $CH_2Cl_2/CH_3OH=8/2$, with the addition of increasing amounts (20 to 50%) of the mixture $CH_2Cl_2/CH_3OH/20\%$ strength aqueous $NH_3=2/4/1$.

The orange-coloured main fraction is evaporated, 2.1 g of 2-mercaptobenzthiazole in 7.5 ml of $CH_3OH/12.5$ ml of $CH_2Cl_2$ are added and the mixture is acidified with 4 N $H_2SO_4$. After adding 5 ml of water to the reaction mixture, the aqueous phase is separated off, extracted twice with 1.5 ml of $CH_2Cl_2$ each time and brought to pH 11 with a basic ion exchanger. After evaporating the aqueous solution, the product remains as a colourless foam.

$R_f=0.48$ ($CH_2Cl_2/CH_3OH/20\%$ strength aqueous $NH_3=2/4/1$).

EXAMPLE 10

1-N-(4-Hydroxybut-2-yl)-sisomicin 250 mg of 4-hydroxybutan-2-one and 12.5 mg of $NaBH_3CN$ are added to 110 mg of 2',3,3'',6'-tetra-N-(o-nitrophenylsulphenyl)-sisomicin in 1.5 ml of tetrahydrofurane and 0.45 ml of water and the pH is brought to 5 with acetic acid. After 30 minutes, the batch is evaporated and the orange-coloured main fraction is isolated by chromatography on silica gel (running agent: $CH_2Cl_2/CH_3OH=99/1$) and thereafter by evaporating off the eluting agent. To split off the protective groups, the substance is dissolved in 0.6 ml of $CH_2Cl_2$, and 68 mg of 2-mercaptobenzthiazole in 0.24 ml of $CH_3OH$ and 0.4 ml of $CH_2Cl_2$ are added, the batch is brought to pH 1 with concentrated $HCl/CH_3OH=1/1$ and is shaken thoroughly with 3 ml of water, the aqueous phase is separated off and is brought to pH 10 with a basic ion exchanger ($OH^-$ form). After filtering off the ion exchanger and evaporating the filtrate in vacuo, the product remains as a colourless foam.

$R_f=0.52$ ($CH_2Cl_2/CH_3OH/20\%$ strength aqueous $NH_3=2/4/1$).

EXAMPLE 11

1-N-(4-Hydroxycyclohex-1-yl)-sisomicin 150 mg of 4-hydroxycyclohexanone and 125 mg of $NaBH_3CN$ are added to 110 mg of 2',3,3'',6'-tetra-N-(o-nitrophenylsulphenyl)-sisomicin in 1.5 ml of tetrahydrofurane/0.45 ml of water, and the mixture is brought to pH 5 with acetic acid. After 1 hour, the batch is worked up to give the end product, as described under Example 10.

$R_f=0.45$ ($CH_2Cl_2/CH_3OH/20\%$ strength aqueous $NH_3=2/4/1$).

EXAMPLE 12

1-N-(Piperidin-4-yl)-sisomicin 1 g of 3''-N-(o-nitrophenylsulphenyl)-2',3,6'-tris-N-trichloroacetylsisomicin is dissolved in 4.5 ml of tetrahydrofurane and 1.5 ml of water, 270 mg of 4-piperidone and 300 mg of $NaBH_3CN$ are added and the mixture is brought to pH 5 with acetic acid. After 48 hours at room temperature the batch is evaporated, the residue is dissolved in 8 ml of $CH_3OH$ and the solution is left to stand with 4 ml of 4 N KOH at room temperature for 2 hours and evaporated again in vacuo. 640 mg of 2-mercaptobenzthiazole in 2.25 ml of $CH_3OH$ and 3.8 ml of $CH_2Cl_2$ are added to the residue, the pH is brought to 1 with concentrated $HCl/CH_3OH=1/1$, 10 ml of H₂O are added, the aqueous phase is separated off and is brought to pH 8 with 2 N NaOH. After evaporation in vacuo, the batch is chromatographed on silica gel and the product with the $R_f$ value 0.44 (running agent: CH₂Cl₂/CH₃OH/20% strength aqueous NH₃=2/4/1) is isolated.

$R_f$=0.44 (CH₂Cl₂/CH₃OH/20% strength aqueous NH₃=2/4/1).

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed:

1. A compound which is a sisomicin derivative of the formula

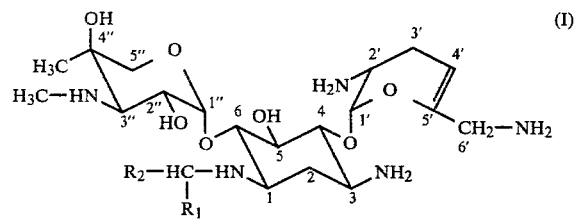

or a pharmaceutically acceptable salt thereof, in which
R₁ is a C₁ to C₆ alkyl group, substituted by hydroxyl, C₁ to C₄ alkoxy, amino, C₁ to C₄ alkylamino, di-C₁ to C₄ alkylamino, C₁ to C₄ alkylcarbonyl, C₁ to C₄ alkylcarbonylamino, N-C₁ to C₄ alkyl-N-C₁ to C₄ alkylcarbonylamino, carboxyl, C₁ to C₄ alkoxy-carbonyl, aminocarbonyl, C₁ to C₄ alkylamino-carbonyl or di-C₁ to C₄ alkylaminocarbonyl and R₂ is C₁ to C₆ alkyl which is unsubstituted or substituted by hydroxyl, C₁ to C₄ alkoxy, amino, C₁ to C₄ alkylamino, di-C₁ to C₄ alkylamino, C₁ to C₄ alkylcarbonyl, C₁ to C₄ alkyl-carbonylamino, N-C₁ to C₄ alkyl-N-C₁ to C₄ alkylcarbonylamino, carboxyl, C₁ to C₄ alkoxycarbonyl, aminocarbonyl, C₁ to C₄ alkylamino-carbonyl or di-C₁ to C₄ alkylaminocarbonyl or radical R₁-C-R₂ denotes a 4-hydroxycyclohex-1-yl group or a piperidin-4-yl group.

2. A compound according to claim 1, in which R₁ denotes a C₁ to C₆ alkyl group which is unsubstituted or substituted by hydroxyl and R₂ denotes a C₁ to C₆ alkyl group which is unsubstituted or substituted by hydroxy or carboxyl.

3. A compound according to claim 1, which is 1-N-(1-Hydroxyprop-2-yl)-sisomicin.

4. A compound according to claim 1, which is 1-N-(1,3-Dihydroxy-prop-2-yl)-sisomicin.

5. A process for the production of a compound according to claim 1, in which a compound of the formula

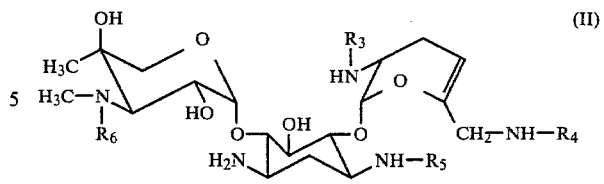

in which
R₃, R₄, R₅ and R₆ independently denote -SR' or -CO-R",
in which
R' denotes an optionally substituted phenyl or di- or tri-phenylmethyl radical and
R" denotes -(CH₂)ₙ₁-B or

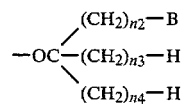

in which
B denotes a hydrogen atom or an optionally substituted phenyl radical, and
n₁, n₂, n₃ and n₄ independently of one another are 0, 1, 2, 3, 4 or 5,
is reacted with a carbonyl compound of the general formula

in which R₁ and R₂ have the same meanings as in claim 1 and in which any amino and alkylamino substituents on R₁ and R₂ are protected by R'-S- or R"-CO- groups, in the presence of a hydrogen donor reducing agent and the protective groups -S-R' or -CO-R" are then split off.

6. A process according to claim 5 which is carried out in an inert organic or inorganic protic solvent.

7. A process according to claim 5 or 6 which is carried out in a pH range of 4 to 8.

8. A process according to claim 7, in which the carbonyl compound of formula (III) is used in ketal form in the presence of a mineral or organic acid.

9. A pharmaceutical composition containing as an active ingredient an antibacterially effective amount of a compound according to claim 1 in admixture with a solid, liquid or liquefied gaseous diluent.

10. A pharmaceutical composition of claim 9 in the form of a sterile or physiologically isotonic aqueous solution.

11. A composition according to claim 9 in the form of ointment, cream or lotion containing from 0.1 to 3.0 g of the said active ingredient per 100 g of ointment, cream or lotion.

12. A medicament in dosage unit form comprising an antibacterially effective amount of a compound according to claim 1 together with an inert pharmaceutical carrier.

13. A medicament of claim 12 in the form of tablets, pills, dragees, capsules, ampoules, or suppositories.

14. A method of combating bacterial infections in warm-blooded animals which comprises administering to the animals an antibacterially effective amount of an active compound according to claim 1 either alone or in admixture with a diluent in the form of medicament.

15. A method according to claim 14, in which the active compound is administered parenterally in an amount of 1 to 15 mg per kg body weight per day.

16. A medicated feed comprising an antibacterial effective amount of a compound according to claim 1 and a nutritious material.

17. A compound according to claim 1 wherein R₁ is hydroxysubstituted C₁ to C₆ alkyl.

* * * * *